(12) United States Patent
Bryant et al.

(10) Patent No.: US 6,395,905 B1
(45) Date of Patent: May 28, 2002

(54) TETRAHYDROINDAZOLE DERIVATIVES AS LIGANDS FOR GABA-A α 5 RECEPTORS

(75) Inventors: Helen Jane Bryant, Roydon; Mark Stuart Chambers, Puckeridge, both of (GB)

(73) Assignee: Merck Sharp & Dohme Ltd., Hertfordshire (GB)

( * ) Notice: Subject to any disclaimer, the term of this patent is extended or adjusted under 35 U.S.C. 154(b) by 0 days.

(21) Appl. No.: 09/868,432

(22) PCT Filed: Jan. 5, 2000

(86) PCT No.: PCT/GB00/00024
§ 371 (c)(1),
(2), (4) Date: Jun. 15, 2001

(87) PCT Pub. No.: WO00/40565
PCT Pub. Date: Jul. 13, 2000

(30) Foreign Application Priority Data

Jan. 6, 1999 (GB) ................................................ 9900222

(51) Int. Cl.[7] ................... C07D 231/56; C07D 401/12; A61K 31/415
(52) U.S. Cl. ................... 548/360.1; 548/275.7; 514/338; 514/406
(58) Field of Search ........................... 548/360.1, 275.7; 514/406, 338

(56) References Cited

FOREIGN PATENT DOCUMENTS

| GB | 2352 632 A | * | 2/2001 |
|----|------------|---|--------|
| WO | WO 95/11885 | | 5/1995 |
| WO | WO 97/34870 | | 9/1997 |
| WO | WO 98/18792 | | 5/1998 |

* cited by examiner

Primary Examiner—Floyd D. Higel
Assistant Examiner—Kamal Saeed
(74) Attorney, Agent, or Firm—J. Eric Thies; Melvin Winokur

(57) ABSTRACT

4-oxo-tetrahydroindozole-3-carboxamide compounds according to Formula (I), or a pharmaceutically acceptable salt thereof, are GABA-A Alpha 5 ligands useful for enhancing cognition:

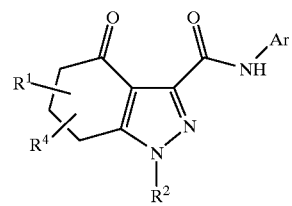

(I)

8 Claims, No Drawings

TETRAHYDROINDAZOLE DERIVATIVES AS LIGANDS FOR GABA-A α 5 RECEPTORS

This is an application under 35 U.S.C. 371 of PCT/GB00/00024 and claims priority from Great Britain Application No. 9900222.2, filed Jan. 6, 1999.

BACKGROUND

SUMMARY OF THE INVENTION

The present invention is directed to 4-oxo-tetrahydroindozole-3-carboxamide compounds according to Formula (I) or a pharmaceutically acceptable salt thereof that are GABA-A Alpha 5 ligands useful for enhancing cognition:

The present invention relates to tetrahydroindazole derivatives, pharmaceutical compositions comprising them and to their use in therapy. More particularly, this invention is concerned with substituted derivatives which are ligands for $GABA_A$ receptors, in particular for $GABA_A$ α5 receptors and are therefore useful in therapy particularly where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the $GABA_A$ α5 receptor subtype.

SUMMARY OF THE INVENTION

The present invention is directed to 4-oxo-tetrahydroindozole-3-carboxamide compounds according to Formula (I) or a pharmaceutically acceptable salt thereof that are GABA-A Alpha 5 ligands useful for enhancing cognition:

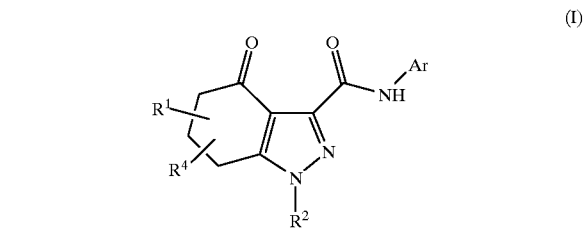

(I)

DETAILED DESCRIPTION OF THE INVENTION

The present invention provides a compound of formula (I) or a pharmaceutically acceptable salt thereof:

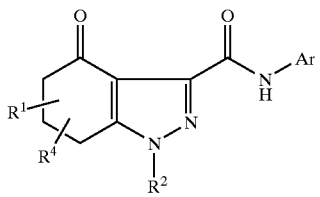

(I)

wherein:
$R^1$ and $R^4$ are independently chosen from hydrogen, halogen, $C_{1-6}$ alkyl, $C_{2-6}$ alkenyl, $C_{2-6}$ alkynyl, $C_{1-6}$ haloalkyl, $C_{2-6}$ haloalkenyl and $C_{2-6}$ haloalkynyl:
$R^2$ is hydrogen or $C_{1-6}$ alkyl; and
Ar is phenyl, a 5-membered heterocyclic group containing 1, 2, 3 or 4 heteroatoms chosen from N, O and S, no more than one of which is O or S, or a 6-membered heterocyclic group containing one or two nitrogen atoms, each of which groups Ar is unsubstituted or substituted by from one to three groups independently chosen from halogen, $C_{1-6}$ alkyl, $C_{2-6}$ alkenyl, $C_{2-6}$ alkynyl, $C_{3-7}$ cycloalkyl, $C_{1-6}$ alkoxy, $C_{2-6}$ alkenyloxy, $C_{2-6}$ alkynyloxy, $C_{3-7}$ cycloalkoxy, $C_{1-6}$ haloalkyl, $C_{2-6}$ haloalkenyl, $C_{2-6}$ haloalkynyl, amino, $C_{1-6}$ alkylamino, di($C_{1-6}$)alkylamino, hydroxy, hydroxy $C_{1-6}$ alkyl, cyano, nitro, amino $C_{1-6}$ alkyl, $C_{1-6}$ alkylamino$C_{1-6}$ alkyl, di($C_{1-6}$ alkyl)amino$C_{1-6}$alkyl or $C_{1-6}$alkoxycarbonylamino$C_{1-6}$alkyl.
$R^1$ is preferably hydrogen, halogen or $C_{1-6}$ alkyl and is particularly hydrogen.
$R^2$ is preferably hydrogen or methyl especially hydrogen.
$R^4$ is preferably hydrogen.
Ar is preferably phenyl or pyridine. When Ar is pyridine it may be 2-pyridine.
Ar is preferably unsubstituted or substituted with one or two groups independently selected from methyl, fluoro, chloro, methoxy, ethoxy, aminomethyl, aminoethyl, hydroxy, methylaminoethyl, dimethylaminoethyl and t-butoxycarbonylaminomethyl, especially from methoxy, fluoro, aminoethyl, methylaminoethyl, dimethylaminoethyl and t-butoxycarbonylaminomethyl.

Specific Examples of compounds according to the present invention are:
4-oxo-4,5,6,7-tetrahydro-1H-indazole-3-carboxylic acid phenylamide;
4-oxo-4,5,6,7-tetrahydro-1H-indazole-3-carboxylic acid-2,5-difluorophenylamide;
4-oxo-4,5,6,7-tetrahydro-1H-indazole-3-carboxylic acid pyridin-2-ylamide;
4-oxo-4,5,6,7-tetrahydro-1H-indazole-3-carboxylic acid 4-methoxyphenylamide; and
4-oxo-4,5,6,7-tetrahydro-1H-indazole-3-carboxylic acid 4-(2-aminoethyl)phenylamide; and the pharmaceutically acceptable salts thereof.

Further specific examples of compounds according to the present invention are:
[N-(4-(2-methylaminoethyl)-phenyl)]-(4-oxo-4,5,6,7-tetrahydro)-1H-indazole-3-carboxamide;
[4-[(4-oxo-4,5,6,7-tetrahydro-1H-indazole-3-carbonyl)amino]benzyl]carbamic acid-tert-butyl ester;
(N-(4-aminomethyl)phenyl))-4-oxo-4,5,6,7-tetrahydro-1H-indazole-3-carboxamide; and
[N-(4-(2-dimethylaminoethyl)phenyl)]-(4-oxo-4,5,6,7-tetrahydro)-1H-indazole-3-carboxamide;

and the pharmaceutically acceptable salts thereof.

There is also provided a pharmaceutical composition comprising a compound of formula I according to the present invention, or a pharmaceutically acceptable salt thereof, and a pharmaceutically acceptable excipient.

Preferably the compositions according to the present invention are in unit dosage forms such as tablets, pills, capsules, powders, granules, solutions or suspensions, or suppositories, for oral, parenteral or rectal administration, by inhalation or insufflation or administration by trans-dermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical venicies. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the $\alpha 5$ subunit. In particular, they are desirably inverse agonists of the $\alpha 5$ subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $_{\alpha}2$ or $\alpha 3$ subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha 5$ subunit, in particular for conditions requiring cognition enhancement such as Alzheimer's disease.

There is also disclosed a method of treatment or prevention of a condition associated with $GABA_A$ receptors containing the $\alpha 5$ subunit which comprises administering to a subject suffering from or prone to such a condition a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl" and "$C_{2-6}$ alkynyl" are to be construed in an analogous manner.

The expression "$C_{3-7}$cycloalkyl" includes cyclopropyl, cyclobutyl, cyclopentyl, cyclohexyl and cycloheptyl groups.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine, especially fluorine, chlorine and bromine.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a process for producing a compound of formula I which comprises reacting a compound of formula II with a compound of formula III:

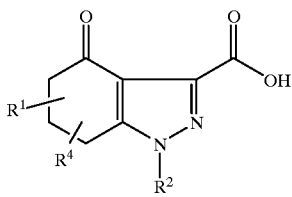

(II)

wherein $R^1$, $R^2$, $R^4$ and Ar are as defined above. The reaction is generally carried out in a mixture of DMF/DCM and in the presence of a coupling agent such as 1-(3-dimethylaminopropyl)-3-ethyl carbodiimide hydrochloride and dimethylaminopyridine. The reaction is generally carried out for about 36 h.

If necessary any reactive portions of the moiety Ar are protected with a protecting group such as tert-butyloxycarbonyl. Such protecting groups can be removed after reaction of the compounds of formulae II and, III to yield a compound of formula I.

The compound of formula II can be made by hydrolyzing a compound of formula IV:

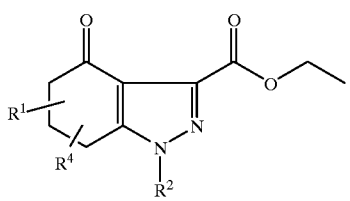

(IV)

wherein $R^1$, $R^2$ and $R^4$ are as defined above, with a base such as NaOH generally by heating at reflux for about 3 h in a solvent such as EtOH.

The compound of formula IV wherein $R^2$ is other than hydrogen can be made by reaction of a compound of formula IV where $R^2$ is hydrogen with a strong base such as Na H followed by alkylation for example with the appropriate alkyl iodide.

The compound of formula IV is made by reacting a compound of formula V with a compound of formula VI:

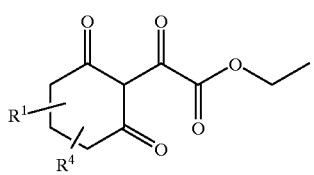

(V)

The compound of formula V is made by reacting a compound of formula VII with a compound of formula VIII:

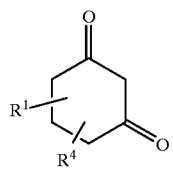

(VII)

wherein $R^1$ and $R^4$ are as defined above and the compound of formula VII is generally pre-reacted with trimethylsilylchloride.

wherein $R^2$ is as defined above, generally in a solvent such as DMF and in the presence of a base such at $Et_3N$ at about 50° C. for about 3 days.

Compounds of formulae III, V, VI, VII and VIII are commercially available or can be made from commercially available compounds by methods known in the art.

The following Examples illustrate pharmaceutical compositions according to the invention.

Composition Example 1A

Tablets Containing 1–25 mg of Compound

|  | Amount mg | | |
| --- | --- | --- | --- |
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

Composition Example 1B

Tablets Containing 26–100 mg of Compound

|  | Amount mg | | |
| --- | --- | --- | --- |
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

Composition Example 2

Parenteral Injection

|  | Amount |
| --- | --- |
| Active Ingredient(s) | 1 to 100 mg |
| Citric Acid Monohydrate | 0.75 mg |

-continued

| | Amount |
|---|---|
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

Composition Example 3

Topical Formulation

| | Amount |
|---|---|
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human GABA$_A$ receptors containing the α5 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillate. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]Ro 15-1788 from the α5 subunit of the human GABA$_A$ receptor of 500 nM or less, preferably of 100 nM or less, and more particularly of 50 nM or less.

More preferably the compounds of the present invention are inverse agonists at the GABA$_A$ α5 subtype whilst being substantially antagonists at the α$_1$, α$_2$ and α$_3$ subtypes. Details of how the effects at the various subtypes can be measured are given in WO-A-9625948.

Further, the present compounds preferably bind preferentially to the GABA$_A$ α5 subtype when compared with the α$_1$, α$_2$ and α$_3$ subtypes. The preferential binding is preferably 5-fold, more preferably 10-fold and most preferably 20-fold.

EXAMPLE 1

4-Oxo-4,5,6,7-tetrahydro-1H-indazole-3-carboxylic acid phenylamide

Step 1: 4-Oxo-4,5,6,7-tetrahydro-1H-indazole-3-carboxylic acid ethyl ester

A solution of 2-ethyloxalylcyclohexan-1,3-dione (6 g, 28 mmol) (Synthesis, 1976, 722) in DMF (3 mL) was treated with hydrazine hydrochloride (1.9 g, 28 mmol) and triethylamine (3.9 mL, 28 mmol) and heated at 50° C. for 3 days. After evaporating to dryness the residue was partitioned between water and DCM and the organic layer separated. The aqueous phase was re-extracted with DCM (×2) and the combined organic layers dried (MgSO$_4$) and evaporated. The residue was purified by column chromatography on silica gel, using MeOH:DCM (2:98) as the eluent, to give an orange solid. The solid was triturated with ether to give the title compound (640 mg, 11%) as a yellow solid. $^1$H NMR (250 MHz, d$_6$-DMSO) δ1.28 (3H, t, J=7.1 Hz), 2.00–2.10 (2H, m), 2.41 (2H, t, J=6.8 Hz), 2.87 (2H, t, J=6.2 Hz), 4.26 (2H, q, J=7.1 Hz), 13.62 (1H, br s). MS, (CI)$^+$209 (M+H)$^+$. Found: C, 57.39; H, 5.76; N, 13.37%. C$_{10}$H$_{12}$N$_2$O$_3$ requires: C, 57.69; H, 5.81; N, 13.45%.

Step 2: 4-Oxo-4,5,6,7-tetrahydro-1H-indazole-3-carboxylic acid

A solution of the foregoing ethyl ester (450 mg, 2.2 mmol) in EtOH (3 mL) and NaOH (4N, 15 mL) was heated at reflux for 3 h. The cooled solution was acidified (conc. HCl), and the resultant solid isolated by filtration and washed with water. The solid was dried at 45° C. in a vacuum oven to give the title compound (265 mg, 67%) as a beige solid. $^1$H NMR (360 MHz, d$_6$-DMSO) δ2.08–2.15 (2H, m), 2.60–2.64 (2H, m), 2.84–2.98 (2H, m), 14.03 (1H, br s). MS. (CI)$^+$181 (M+H)$^+$. Found: C, 52.33; H, 4.24; N, 15.00%. C$_8$H$_8$N$_2$O$_3$. 0.2H$_2$O requires: C, 52.29; H, 4.61; N, 15.24%.

Step 3: 4-Oxo-4,5,6,7-tetrahydro-1H-indazole-3-carboxylic acid phenylamide

A suspension of the foregoing carboxylic acid (100 mg, 0.55 mmol) in DMF (2 mL) and DCM (5 mL) was treated with 1-(3-dimethylaminopropyl)-3-ethyl carbodiimide hydrochloride (160 mg, 0.83 mmol), 4-dimethylaminopyridine (101 mg, 0.83 mmol) and aniline (77 mg, 0.83 mmol). The resultant solution was stirred for 36 h then diluted with DCM (20 mL) and washed with water (×1), 1N HCl (×2), sat. NaHCO$_3$ (×1) and water (×1). The organic layer was dried (MgSO$_4$) and evaporated. The residue was purified by column chromatography on silica gel, eluting with DCM:MeOH (97:3) to give the title compound (90 mg, 64%) as a colourless solid. mp 244° C. (dec.). $^1$H NMR (500 MHz, d$_6$-DMSO) δ2.09–2.14 (2H, m), 2.63–2.67 (2H, m), 2.80–2.95 (2H, m), 7.05–7.15 (1H, m) 7.30–7.40 (2H, m), 7.70–7.75 (2H, m) 12.24 (1H, br s), 13.68 and 14.20 (1H, 2×br s) MS. (CI)$^+$256 (M+H)$^+$. Found: C, 64.22; H, 5.00; N, 15.97%. C$_{14}$H$_{13}$N$_3$O$_2$.0.3H$_2$O requires: C, 64.51; H, 5.26; N, 16. 12%.

EXAMPLE 2

4-Oxo-4,5,6,7-tetrahydro-1H-indazole-3-carboxylic acid-2,5-difluorophenylamide

The title compound was obtained using the procedure described in Example 1, Step 3 using 2,5-difluoroaniline. The amide (15 mg, 19%) was isolated as a colourless solid. $^1$H NMR (400 MHz, d$_6$-DMSO) δ2.05–2.15 (2H, m), 2.60–2.68 (2H,m), 2.85–2.98 (2H, br s), 6.92–7.04 (1H, m), 7.30–7.40 (1H, m), 8.20–8.28 (1H, m), 12.43 (1H, br s), 13.83 and 14.35 (1H, 2×br s). MS, (CI)$^+$292 (M+H)$^+$.

EXAMPLE 3

4-Oxo-4,5,6,7-tetrahydro-1H-indazole-3-carboxylic acid pyridin-2-ylamide

The title compound was obtained using the procedure described in Example 1, Step 3 using 2-aminopyridine. The amide (33 mg, 46%) was isolated as a cream solid. mp 250° C. (dec.). $^1$H NMR (400 MHz, d$_6$-DMSO) δ2.05–2.15 (2H, m), 2.62 (2H, t, J=6.2 Hz), 2.85–2.95 (2H, br s). 7.10–7.20 (1H, m), 7.78–7.88 (1H, m), 8.24 (1H, d, J=8.3 Hz), 8.35–8.41 (1H, m), 12.55 (1H, s), 13.78 and 14.26 (1H, 2×br s). Found: C, 60.34; H, 4.34; N, 21.19%. C$_{13}$H$_{12}$N$_4$O$_2$.0.05 CH$_2$Cl$_2$ requires: C, 60.17; H, 4.68; N, 21.51%. MS (CI)$^+$ 257 (M+H)$^+$.

EXAMPLE 4

4-Oxo-4,5,6,7-tetrahydro-1H-indazole-3-carboxylic acid 4-methoxyphenylamide

The title compound was obtained using the procedure described in Example 1, Step 3 using p-anisidine. The amide (15 mg, 19%) was isolated as a beige solid. $^1$H NMR (400 MHz, d$_6$-DMSO) δ2.07–2.13 (2H, m), 2.63 (2H, t, J=6.3 Hz), 2.82–2.94 (2H, m), 3.76 (3H, s), 6.95 (2H, d, J=8.9 Hz), 7.63 (2H, dd, J=6.8 and 2.1 Hz), 12.14 (1H, br s), 13.65 and 14.20 (1H, 2×br s). MS, (CI)$^+$: 286 (M+H)$^+$.

EXAMPLE 5

4-Oxo-4,5,6,7-tetrahydro-1H-indazole-3-carboxylic acid 4-(2-aminoethyl)phenylamide Step 1: 2-(4-Aminophenyl)ethyl carbamic acid tert-butyl ester A solution of 2-(4-aminophenyl)ethylamine (1 g, 7.3 mmol) in DCM (20 mL) at room temperature was treated with triethylamine (0.82 g, 7.7 mmol). After 10 min the solution was cooled to –5° C. Di-tert-butyldicarbonate (1.68 g, 7.7 mmol) was added portionwise over 10 min and stirred for 30 min before warming to room temperature. NaHCO$_3$ (sat. 2 mL) was added followed by water (40 mL). The organic layer was separated and aqueous re-extracted with DCM (×2). The combined organic layers were dried (K$_2$CO$_3$) and evaporated. The residue was purified by column chromatography on silica gel, eluting with EtOAc:hexane (1:4) to obtain the title compound (1.4 g, 80%) as a yellow solid. 1H NMR (360 MHz, d$_6$-DMSO) δ1.37 (9H, s), 2.49–2.51 (2H, m), 2.99–3.06 (2H, m), 4.83 (2H, s), 6.49 (2H, d, J=8.3 Hz), 6.77–6.80 (1H, m), 6.81 (2H, d, J=8.3 Hz) MS (CI)$^+$237 (M+H)$^+$.

Step 2: [2[4-(4-Oxo-4,5,6,7-tetrahydro-1H-indazole-3-carbonyl)amino]phenyl]ethyl carbamic acid tert-butyl ester The title compound was obtained using the procedure described in Example 1, Step 3 using the foregoing amine. The residue was purified by column chromatography on silica gel, eluting with DCM:MeOH (97:3) to give the amide (100 mg, 45%) and was isolated as a colourless, low-melting solid. H NMR (400 MHz, d$_6$-DMSO) 1.37 (9H, s), 2.07–2.14 (2H, m), 2.63 (2H, t, J=6.4 Hz), 2.69 (2H, t, J=7.1 Hz), 2.89 (2H, t, J=6.2 Hz), 3.13–3.19 (2H, m), 6.52–6.65 (1H, m), 7.20 (2H, d, J=8.3 Hz), 7.63 (2H, d, J=8.4 Hz), 12.18 (1H, s), 14.00 (1H, br s).

Step 3: 4-Oxo-4,5,6,7-tetrahydro-1H-indazole-3-carboxylic acid 4-(2-aminoethyl)phenylamide A suspension of the foregoing carbamate (100 mg, 0.25 mmol) in DCM (5 mL) was treated with trifluoroacetic acid (0.5 mL) and stirred at room temperature for 5 h. The mixture was evaporated and residue partitioned between water and MeOH/DCM (5:95) and neutralised with NaHCO$_3$ (sat.). The organic layer was separated and the aqueous phase re-extracted with MeOH/DCM (5:95) (×2). The combined organic layers were dried (K$_2$CO$_3$) and evaporated. The residue was purified using column chromatography on silica gel, eluting MeOH:DCM (10:90) followed by DCM:MeOH:NH$_3$ (80:20:1). The title compound (35 mg, 47%) was isolated as a cream solid. mp 250° C. (dec.). $^1$H NMR (360 MHz, d$_6$-DMSO) δ2.06–2.14 (2H, m), 2.63 (2H, t, J=6.7 Hz), 2.68 (2H, t, J=6.9 Hz), 2.84 (2H, t, J=7.6 Hz), 2.89 (2H, t, J=6.4 Hz), 7.24 (2H, d, J=8.4 Hz), 7.67 (2H, d, J=8.5 Hz), 12.39 (1H, s). MS, (CI)$^+$299 (M+H)$^+$.

EXAMPLE 6

[N-(4-(2-Methylaminoethyl)-phenyl)]-(4-oxo-4,5,6, 7-tetrahydro)-1H-indazole-3-carboxamide Step 1: Methyl-[2-(4-nitrophenyl)ethyl]carbamic acid tert-butyl ester The title compound was obtained using the procedure described in Example 5, Step 1 using N-methyl-2-(4-nitrophenyl)ethylamine. The title compound (3 g) was isolated as a yellow oil which was used without further purification. $^1$H NMR (400 MHz, CDCl$_3$) δ1.39 (9H, s), 2.83 (3H, s), 2.88–2.96 (2H, m), 3.48 (2H, t, J=6.5 Hz), 7.30–7.40 (2H, m), 8.15 (2H, d, J=8.3 Hz).

Step 2: [2-(4-Aminophenyl)ethyl]-methyl-carbamic acid tert-butyl ester

A solution of the foregoing nitro derivative (3 g), in EtOAc (20 mL) and EtOH (20 mL) was treated with a slurry of 10% Pd on C (200 mg) in water (5 mL). The mixture was shaken on parr apparatus at 50 psi $H_2$ for 15 min. after which time no further $H_2$ was consumed. The catalyst was removed by filtration and the solvents evaporated to give title compound (2.2 g, 94%) as a pale orange oil. $^1$H NMR (360 MHz, $CDCl_3$) δ1.42 (9H, s), 2.68 (2H, t, J=7.2 Hz), 2.80 (3H, s), 3.35 (2H, t, J=6.4 Hz), 6.63 (2H, d, J=8.3 Hz), 6.92–7.02 (2H, s).

Step 3: Methyl-(2-{4-[(4-oxo-4,5,6,7-tetrahydro-1H-indazole-3-carbonyl)-amino]phenyl}ethyl)-carbamic acid isobutyl ester A suspension of 4-oxo-4,5,6,7-tetrahydro-1H-indazole-3-carboxylic acid (200 mg, 1.1 mmol) in isobutyl chloroformate (10 mL) was treated with $Et_3N$ (0.46 mL, 3.3 mmol) portionwise at room temperature. After 30 min. further $Et_3N$ (0.46 mL, 3.3 mmol) was added and the mixture stirred for 30 min. The mixture was evaporated and residue suspended in 1,2-DCE (15 mL). The foregoing amine (0.37 g, 1.7 mmol) added and the solution was heated at reflux for 6 h. The solvent was evaporated, the residue suspended in EtOH (1.5 mL) and then treated with 4N NaOH (5 mL). The mixture was heated at reflux for 1 h. Water (50 mL) was added to the cooled mixture, the aqueous phase extracted with 10% MeOH/DCM (×3) and the combined organic layers dried ($MgSO_4$) and evaporated. The residue was purified by silica plug chromatography, using MeOH:DCM (6:94) as eluent, to give title compound (250 mg, 54%) a cream solid. $^1$H NMR (400 MHz, $CDCl_3$) δ0.94 (6H, d, J=6.4), 1.88–1.98 (2H, m), 2.19–2.27 (2H, m), 2.7 (2H, t, J=6.1 Hz), 2.77–2.92 (5H, m), 2.98 (2H, t, J=5.8 Hz), 3.40–3.51 (2H, m), 3.85 (2H, d, J=6.44 Hz), 7.18–7.26 (2H, m), 7.74 (2H, d, J=7.9 Hz), 11.30 (1H, br, s), 12.26 (1H, s). MS, $(CI)^+$413 $(M+H)^+$.

Step 4: [N-(4-(2-Methylaminoethyl)phenyl)](4-oxo-4 5,6,7-tetrahydro)-1H-indazole-3-carboxamide A solution of the foregoing carbamate (150 mg, 0.36 mmol) in 45% HBr in acetic acid solution (10 mL) was heated in a sealed tube at 85° C. for 6 h. After cooling the solution was diluted with water and basified with 4N NaOH. The organic solvent was evaporated and residue extracted with 10% MeOH/DCM (×4). The combined organic layers were washed with water, dried ($MgSO_4$) and concentrated to give a white solid. The solid was triturated with ether and isolated by filtration. Title compound (70 mg, 58%) was isolated as a white solid. $^1$H NMR (360 MHz, $d_6$. DMSO) δ2.05–2.15 (2H, m), 2.32 (3H, s), 2.64 (2H, t, J=5.9 Hz), 2.67–2.78 (4H, m), 2.88 (2H, t, J=6.2 Hz), 7.24 (2H, d, J=8.4 Hz), 7.65 (2H, d, J=8.5 Hz), 12.36 (1H, s). MS, $(CI)^+$313 $(M+H)^+$.

EXAMPLE 7

[4-[(4-Oxo-4,5,6,7-tetrahydro-1H-indazole-3-carbonyl)amino]benzyl]carbamic acid-tert-butyl ester Step 1: (4-Nitrobenzyl)carbamic acid-tert-butyl ester A solution of 4-nitrobenzylamine hydrochloride (5 g, 0.026 mol) in DCM (300 mL) was treated with $Et_3N$ (4.0 mL, 0.029 mol) and stirred at room temperature for 15 min. A solution of di-tert-butyldicarbonate (5.95 g, 0.027 mol) in DCM (50 mL) was then added and the solution stirred for 3 h. After this time the mixture was filtered and the filtrate evaporated. The residue was treated with EtOAc, filtered and the filtrate washed with citric acid (10%, 100 mL). The organic layer was separated, dried ($MgSO_4$) and evaporated. The residue was treated with petrol:EtOAc (2:1) and the resultant colourless solid (3.44 g, 53%) collected by filtration.

Step 2: (4-Aminobenzyl)carbamic acid tert-butyl ester

A solution of the foregoing nitro derivative (1.05 g, 4.2 mmol) in EtOH (100 mL) was hydrogenated at 25 psi for 20 min. in the presence of 10% Pd on C (200 mg). The catalyst was removed by filtration and the solvent evaporated in vacuo. The residue was treated with ether, the mixture filtered and the filtrate evaporated. The residue was chromatographed on silica gel, eluting with petrol:$Et_2O$ (1:1) followed by petrol:EtOAc (1:1). The title compound (452 mg, 48%) was isolated as a colourless solid. $^1$H NMR (360 MHz, $CDCl_3$) δ1.45 (9H, s), 3.55–3.69 (2H, m), 4.18 (2H, d, J=5.4 Hz), 4.7 (2H, br, s), 6.64 (2H, d, J=8.4 Hz), 7.07 (2H, d, J=8.2 Hz). $MS(ES^+)$ 223 (M+1).

Step 3: [4-[(4-Oxo-4,5,6,7-tetrahydro-1H-indazole-3-carbonyl)amino]benzyl]carbamic acid-tert-butyl ester The title compound was obtained using the procedure described in Example 1, Step 3 using the foregoing amine. The amide (130 mg, 40%) was isolated as a cream solid. $^1$H NMR (400 MHz, $CDCl_3$) δ1.46 (9H, s), 2.18–2.27 (2H, m), 2.70 (2H, t, J=5.9 Hz), 2.98 (2H, t, J=5.9 Hz), 4.30 (2H, s, J=4.8 Hz), 4.80–4.88 (1H, m), 7.30 (2H, d, J=8.1 Hz), 7.78 (2H, d, J=8.0 Hz), 11.25 (1H, br, s), 12.30 (1H, s). MS, $(CI)^+$385 $(M+H)^+$.

EXAMPLE 8

(N-(4-Aminomethyl)phenyl))-4-oxo-4,5,6,7-tetrahydro-1H-indazole-3-carboxamide

The title compound was obtained using the procedure described in Example 5, Step 3 using [4-[(4-oxo-4,5,6,7-tetrahydro-1H-indazole-3-carbonyl)amino]benzyl]carbamic acid-tert-butyl ester. The residue was triturated with 1:1 DCM/$Et_2O$ to obtain title compound (35 mg, 47%) as a white solid. $^1$H NMR (360 MHz, $d_6$ DMSO) δ2.05–2.13 (2H, m), 2.64 (2H, t, J=6.7 Hz), 2.88 (2H, t, J=6.2 Hz), 3.73 (2H, s), 7.36 (2H, d, J=8.5 Hz), 7.68 (2H, d, J=8.5 Hz), 12.39 (1H, s). MS $(CI^+)$ 285 $(M+H)^+$.

EXAMPLE 9

[N-(4-(2-Dimethylaminoethyl)phenyl)]-(4-oxo-4,5,6,7-tetrahydro)-1H-indazole-3-carboxamide Step1: 2-(4-Aminophenyl)N,N-dimethylacetamide A suspension of 4-aminophenylacetic acid (5 g, 30 mmol), 1-(3-dimethylaminopropyl)-3-ethyl carbodiimide hydrochloride (6.9 g, 36 mmol), and dimethylamine (6.5 mol of a 5.6M solution in EtOH 36 mmol) in 1,2, DCE was stirred at room temperature for 4 h. Silica was added, the suspension evaporated and residue loaded onto silica plug column, eluting with DCM:MeOH/98:2). The title compound (2.6 g, 45%) was isolated as an orange solid. $^1$H MNR (400 MHz, $CDCl_3$) δ2.94 (3H, s), δ2.98 (3H, s), 3.60 (2H, s), 6.64 (2H, d, J=8.3 Hz), 7.03 (2H, d, 8.2 Hz). MS $(CI)^+$179 $(M+H)^+$.

Step 2: 4-(2-Dimethylaminoethylaniline

A solution of the foregoing amide (100 mg, 0.56 mmol) in THF (10 mL) was treated with $LiAlH_4$ (1.68 mL of a 1M solution in THF, 1.68 mmol) and the resultant mixture heated at reflux for 16 h. Water (0.05 mL) was added followed by 4N NaOH (0.05 mL) then water (0.05 mL). The suspension was filtered and solvents evaporated. The title compound (80 mg) was isolated as a red oil. $^1$H NMR (400 MHz, CDCl$_3$) δ2.31 (6H, s), 2.45–2.49 (2H, m), 2.65–2.69 (2H, m), 3.54 (2H, s), 6.62 (2H, d, J=8.2 Hz), 6.99 (2H, d, J=8.2 Hz). MS (CI)$^+$165 (M+H)$^+$.

Step 3: [N-(4-(2-Dimethylaminoethyl)phenyl)](4-oxo-4,5,6,7-tetrahydro-1H-indazole-3-carboxamide The title compound was obtained using the procedure described Example 1, Step 3, using the foregoing amine (84 mg, 0.51 mmol) but heating at reflux for 15 h. Silica was added and the mixture was evaporated. The residue was loaded onto silica plug column and title compound eluted with DCM:MeOH:25% NH$_3$OH (89:10:1) (6 mg, 4%) as an orange solid. $^1$H NMR (400 MHz, CDCl$_3$) δ2.19–2.28 (2H, m), 2.32 (6H, s), 2.54–2.61 (2H, m), 2.69 (2H, t, J=6.7 Hz), 2.77–2.82 (2H, m), 2.98 (2H, t, J=6.1 Hz), 7.22 (2H, d, J=8.3 Hz), 7.72 (2H, d, J=8.4 Hz). MS (CI)$^+$327 (M+H)$^+$.

What is claimed is:

1. A compound of formula (I) or a pharmaceutically acceptable salt thereof:

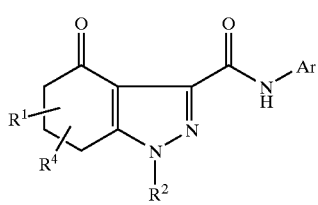

(I)

wherein:

$R^1$ and $R^4$ are independently chosen from hydrogen, halogen, $C_{1-6}$ alkyl, $C_{2-6}$ alkenyl, $C_{2-6}$ alkynyl, $C_{1-6}$ haloalkyl, $C_{2-6}$ haloalkenyl and $C_{2-6}$ haloalkynyl:

$R^2$ is hydrogen or $C_{1-6}$ alkyl; and

Ar is phenyl, a 5-membered heterocyclic group containing 1, 2, 3 or 4 heteroatoms chosen from N, O and S, no more than one of which is O or S, or a 6-membered heterocyclic group containing one or two nitrogen atoms, each of which groups Ar is unsubstituted or substituted by from one to three groups independently chosen from halogen, $C_{1-6}$ alkyl, $C_{2-6}$ alkenyl, $C_{2-6}$ alkynyl, $C_{3-7}$ cycloalkyl, $C_{1-6}$ alkoxy, $C_{2-6}$ alkenyloxy, $C_{2-6}$ alkynyloxy, $C_{3-7}$ cycloalkoxy, $C_{1-6}$ haloalkyl, $C_{2-6}$ haloalkenyl, $C_{2-6}$ haloalkynyl, amino, $C_{1-6}$ alkylamino, di($C_{1-6}$)alkylamino, hydroxy, hydroxy $C_{1-6}$ alkyl, cyano, nitro, amino $C_{1-6}$ alkyl, $C_{1-6}$ alkylamino$C_{1-6}$ alkyl, di($C_{1-6}$ alkyl)amino$C_{1-6}$alkyl or $C_{1-6}$alkoxycarbonylamino$_{1-6}$alkyl.

2. A compound according to claim 1 wherein Ar is unsubstituted or substituted by from one to three groups independently chosen from halogen, $C_{1-6}$ alkyl, $C_{2-6}$ alkenyl, $C_{2-6}$ alkynyl, $C_{3-7}$ cycloalkyl, $C_{1-6}$ alkoxy, $C_{2-6}$ alkenyloxy, $C_{2-6}$ alkynyloxy, $C_{3-7}$ cycloalkoxy, $C_{1-6}$ haloalkyl, $C_{2-6}$ haloalkenyl, $C_{2-6}$ haloalkynyl, amino, $C_{1-6}$ alkylamino, di($C_{1-6}$)alkylamino, hydroxy, hydroxy $C_{1-6}$ alkyl, cyano, nitro, amino $C_{1-6}$ alkyl, $C_{1-6}$ alkylamino$C_{1-6}$ alkyl or di($C_{1-6}$ alkyl)amino$C_{1-6}$alkyl.

3. A compound according to claim 1 wherein $R^1$ is hydrogen, halogen or $C_{1-6}$alkyl;

$R^2$ is hydrogen or methyl; and $R^4$ is hydrogen.

4. A compound according to claim 1 wherein Ar is phenyl or pyridine and is unsubstituted or substituted with one or two groups independently selected form methyl, fluoro, chloro, methoxy, ethoxy, aminomethyl, aminoethyl, hydroxy, methylaminoethyl, dimethylaminoethyl, and t-butoxycarbonylaminomethyl.

5. A compound according to claim 1 selected from 4-oxo-4,5,6,7-tetrahydro-1H-indazole-3-carboxylic acid phenylamide;

4-oxo-4,5,6,7-tetrahydro-1H-indazole-3-carboxylic acid-2,5-difluorophenylamide;

4-oxo-4,5,6,7-tetrahydro-1H-indazole-3-carboxylic acid pyridin-2-ylamide;

4-oxo-4,5,6,7-tetrahydro-1H-indazole-3-carboxylic acid 4-methoxyphenylamide;

4-oxo-4,5,6,7-tetrahydro-1H-indazole-3-carboxylic acid 4-(2-aminoethyl)phenylamide;

[N-(4-(2-methylaminoethyl)-phenyl)]-(4-oxo-4,5,6,7-tetrahydro)-1H-indazole-3-carboxamide;

[4-[(4-oxo-4,5,6,7-tetrahydro-1H-indazole-3-carbonyl)amino]benzyl]carbamic acid-tert-butyl ester;

(N-(4-aminomethyl)phenyl))-4-oxo-4,5,6,7-tetrahydro-1H-indazole-3-carboxamide; and

[N-(4-(2-dimethylaminoethyl)phenyl)]-(4-oxo-4,5,6,7-tetrahydro)-1H-indazole-3-carboxamide;

and a pharmaceutically acceptable salt thereof.

6. A pharmaceutical composition comprising a compound according to claim 1 or a pharmaceutically acceptable salt thereof, and a pharmaceutically acceptable excipient.

7. A process for the preparation of a pharmaceutical composition which comprises adding a compound according to claim 1 or a pharmaceutically acceptable salt thereof to a pharmaceutically acceptable excipient.

8. A method of treatment of a condition associated with GABA$_A$ receptors containing the α5 subunit which comprises administering to a subject suffering from or prone to such a condition a therapeutically or prophylactically effective amount of a compound of claim 1 or a pharmaceutically acceptable salt thereof.

* * * * *